United States Patent [19]

Heitkämper et al.

[11] 4,388,238

[45] Jun. 14, 1983

[54] PROCESS FOR THE PREPARATION OF N,O-DISUBSTITUTED URETHANES SUITABLE AS A STARTING MATERIAL FOR THE PREPARATION OF ISOCYANATES

[75] Inventors: Peter Heitkämper, Dormagen; Klaus König, Leverkusen; Rudolf Fauss, Cologne; Kurt Findeisen, Odenthal, all of Fed. Rep. of Germany

[73] Assignee: Bayer Aktiengesellschaft, Leverkusen, Fed. Rep. of Germany

[21] Appl. No.: 197,042

[22] Filed: Oct. 15, 1980

[30] Foreign Application Priority Data

Oct. 27, 1979 [DE] Fed. Rep. of Germany ....... 2943480

[51] Int. Cl.$^3$ .............. C07C 125/065; C07C 125/073; C07C 125/077
[52] U.S. Cl. ................. 260/239 E; 260/404; 260/465.4; 260/938; 544/164; 544/322; 544/332; 546/312; 546/335; 548/163; 548/361; 549/461; 560/22; 560/24; 560/25; 560/27; 560/28; 560/29; 560/30; 560/31; 560/32; 560/33; 560/115; 560/157; 560/158; 560/160; 560/162; 560/166; 560/167

[58] Field of Search ........................ 560/24, 25, 22, 27, 560/28, 30, 29, 31, 32, 115, 157, 158, 160, 162, 166, 167, 33; 260/465.4, 465 D, 239 E, 938, 346.71, 404; 544/164, 322, 332; 546/312, 334, 335; 549/28, 461; 548/378, 163, 361

[56] References Cited

U.S. PATENT DOCUMENTS 2,409,712 10/1946 Schweitzer ..................... 260/453
2,806,051  9/1957 Brockway ...................... 260/471
4,278,805  7/1981 Merger et al. .................. 560/25

Primary Examiner—Michael L. Shippen
Attorney, Agent, or Firm—Gene Harsh; Joseph C. Gil; Lyndanne M. Whalen

[57] ABSTRACT

A process for the preparation of N,O-disubstituted urethanes. Primary amines and alcohols are reacted with organic compounds having carbonyl groups at 120° to 350° C. Suitable carbonyl-containing compounds include N-unsubstituted urethanes. N-mono-substituted, N,N'-disubstituted ureas, or polyureas may be used in combination with the N-unsubstituted urethane. The product urethanes are particularly suitable for the preparation of isocyanates.

6 Claims, No Drawings

PROCESS FOR THE PREPARATION OF N,O-DISUBSTITUTED URETHANES SUITABLE AS A STARTING MATERIAL FOR THE PREPARATION OF ISOCYANATES

BACKGROUND OF THE INVENTION

The present invention relates to an improved process for the preparation of urethanes by reacting primary amines, alcohols, and organic compounds which have carbonyl groups. N-unsubstituted urethanes and optionally N-mono- or N,N'-disubstituted ureas or polyureas are used as the organic compounds having carbonyl groups.

N,O-disubstituted urethanes may be prepared by reacting organic isocyanates with alcohols. This reaction is reversible, i.e., the urethanes, once produced, can be thermally dissociated into the isocyanate and the alcohol from which they were derived. One such dissociation reaction is described in U.S. Pat. No. 2,409,712. Urethanes which can be thermally dissociated into isocyanates are, therefore, potential starting materials for the preparation of these isocyanates. Until now, such isocyanates had been almost universally prepared by reaction of primary amines with phosgene. The preparation of urethanes without the use of phosgene in a manner which avoids subsequent thermal dissociation of the product urethane would, however, provide a valuable alternative to the commercially used process.

Urethanes have been prepared without phosgene by reacting urea with amines and alcohol (see, for example, U.S. Pat. Nos. 2,409,712 or 2,806,051). However, these prior art processes produce urethanes in insufficient amounts and in an impure form.

SUMMARY OF THE INVENTION

It is an object of the present invention to provide a process for the production of N,O-disubstituted urethanes in which primary amines, alcohols and organic carbonyl compounds are reacted. It is a further object of the present invention to provide a novel process for the preparation of urethanes by reacting primary amines and alcohols with organic carbonyl compounds, which produces N,O-disubstituted urethanes in good yield and in a substantially pure form.

These and other objects which will be apparent to those skilled in the art are achieved by reacting N-unsubstituted urethanes and optionally N-mono-substituted or N,N-disubstituted ureas or polyureas with a primary amine and an alcohol.

DETAILED DESCRIPTION OF THE PREFERRED EMBODIMENTS

The present invention is a process for the preparation of N,O-disubstituted urethanes by reacting primary amines and alcohols with organic compounds having carbonyl groups at a temperature of from 120° to 350° C. The organic compounds which have carbonyl groups are N-unsubstituted urethanes and optionally N-monosubstituted or N,N'-disubstituted ureas or polyureas.

The process according to the invention is particularly suitable for the preparation of urethanes having the general formula

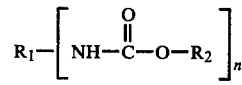

in which $R_1$ represents a substituted or unsubstituted aliphatic hydrocarbon radical having from 1 to 18 carbon atoms; a substituted or unsubstituted cycloaliphatic hydrocarbon radical having from 3 to 18 carbon atoms; a substituted or unsubstituted aromatic hydrocarbon radical having from 6 to 15 carbon atoms; a substituted or unsubstituted araliphatic hydrocarbon radical having from 7 to 14 carbon atoms, or a substituted or unsubstituted 5- or 6-membered heterocyclic radical, which can also be fused with a benzene ring;

$R_2$ represents a substituted or unsubstituted alkyl radical having from 1 to 20 carbon atoms; a substituted or unsubstituted cycloalkyl radical having from 3 to 16 carbon atoms; or a substituted or unsubstituted aralkyl radical having from 7 to 14 carbon atoms; and n represents an integer from 1 to 3.

Where n=2 or 3, at least two carbon atoms should be positioned between the two urethane groups bonded to the radical R.

The following are suitable substituents of the aliphatic or cycloaliphatic radicals $R_1$ or $R_2$: $C_6$–$C_{10}$-aroxy-; $C_1$–$C_6$-alkoxy-; $C_1$–$C_6$-alkoxy-$C_2$–$C_4$-alkoxy; $C_1$–$C_6$-acyl-; $C_1$–$C_6$-alkylmercapto-; $C_6$–$C_{10}$-arylmercapto-; $C_1$–$C_{12}$-alkylcarbonyl-; di-($C_1$–$C_8$-alkyl)-amino-; $C_1$–$C_6$-acylamino-, nitro-, cyano or rhodano-radicals. Suitable substituents for the aromatic or araliphatic radicals $R_1$ or $R_2$ include: $C_1$–$C_{12}$-alkyl-; $C_1$–$C_{12}$-alkylsulphonyl-; $C_6$–$C_{10}$-arylsulphonyl-; $C_1$–$C_{12}$-alkylsulphonic acid ester of sulphonamide radicals.

The preferred products of the present invention are those corresponding to the general formula in which $R_1$ represents an aliphatic hydrocarbon radical having from 3 to 18 carbon atoms; a cycloaliphatic hydrocarbon radical having from 6 to 15 carbon atoms; or an aromatic hydrocarbon radical, having from 6 to 15 carbon atoms, which may be methyl, methoxy or chlorine substituted and/or have methylene bridges;

$R_2$ represents a $C_1$–$C_4$-alkoxy-substituted or $C_1$–$C_4$-alkoxy-$C_2$–$C_4$-alkoxy-substituted or unsubstituted aliphatic hydrocarbon radical having from 1 to 18 (preferably from 1 to 4) carbon atoms, which radical is obtained by removing the hydroxyl group from a monohydric unsubstituted primary or secondary aliphatic alcohol; or a cyclohexyl or 2-phenyl-ethyl radical; and n represents 1 or 2.

Primary amines of the formula

wherein $R_1$ and n are as defined above, are appropriate starting materials for the process of the present invention.

Examples of suitable amines are methylamine; ethylamine; propylamine; isopropylamine; butylamine; isobutylamine; tert.-butylamine; hexylamine; dodecylamine; 2-ethylhexylamine; tetradecylamine; hexadecylamine; octadecylamine; allylamine; 1,4-diaminobutane; 1,6-diaminohexane; 2,5-dimethyl-2,5-hexane diamine; trimethylhexamethylene diamine; 2-methoxyethylamine; 3-ethoxypropylamine; 3-butoxypropylamine; 1,4-butanediol-bis-(3-aminopropylether); 3-aminopropanic acid-2-methyl propylester; 6-amino-hexane nitrile; lysine ester; 1,1-aminoundecane acid ester; cyclohexylamine; trimethylcyclohexylamine; 2-norbornylmethylamine; aniline; o-, m- or p-chloroaniline; 2,3-, 2,4-, 2,5- or 2,6-dichloroaniline; 3,4-dichloroaniline; p- or o-nitroaniline; m-, o- or p-tolylamine; 3-trifluoromethylaniline; 3-chloro-4-methylaniline; benzylamine; phenylcyclohexylamine; naphthylamine; 1,4-diaminocyclohexane; 2,4- or 2,6-diamino-1-methylcyclohexane; 5-amino-1-aminomethyl 1,3,3-trimethylcyclohexane; 4,4'-diaminodicyclohexylmethane; 4,4'-diamino-3,3'-dimethyl-dicyclohexylmethane; 1,3-diaminobenzene; 1,4-diaminobenzene; 2-chloro-1,4-diaminobenzene; 2,4-diaminotoluene; 2,6-diaminotoluene (and mixtures with 2,4-); 2-(n-ethyl-amino)-4-aminotoluene; 1,3-diamino-2-methylbenzene; 1,3-bisaminomethylbenzene; 1,3-bisaminomethyl-4,6-dimethylbenzene; 1,3-diamino-2,6-(4,6)-diethyl-4-methylbenzene; 1,3-diamino-2,4,6-triisopropylbenzene; 1,5-diaminonaphthalene; 2,7-diamino-naphthalene; benzidine; 3,3'-dichlorobenzidine; 4,4'-diaminodiphenylmethane (and crude substances); 3,3'-dichloro-4,4'-diaminodiphenylmethane; 2,2-bis-(4-aminophenyl)-propane; 1,1-bis-(4-aminophenyl)-cyclohexane; 1,1-bis-(4-amino-3-methylphenyl)-cyclohexane; 4,4',4''-triaminotriphenylmethane; 4,4'-diaminodiphenylether; 4,4',4''-triaminotriphenylthiophosphate; p-methoxyaniline; p-ethoxyaniline; 1-(4-chlorophenoxy)-4-aminobenzene; 2,4-diaminodiphenylether; m-aminobenzoic acid ester; p-aminobenzoic acid ester; 3,5-diamino-2-methyldiphenylmethane; 3,5-diamino-4-methyl-diphenylmethane (and mixtures); 3,5-diamino-4-methyl-dicyclohexylmethane; 3,5-diamino-2-methyl-dicyclohexylmethane (and mixtures); 3,5,4'-triamino-4-methyl-diphenylmethane; 3,5,4'-triamino-2-methyl-diphenylmethane; 3,5,2'-triamino-4-methyl-diphenyl-methane; 3,5,2'-triamino-2-methyl-diphenylmethane (and mixtures); 3,5,4'-triamino-4-methyl-dicyclohexylmethane; 3,5,4'-triamino-2-methyl-dicyclohexylmethane; 3,5,2'-triamino-4-methyl-dicyclohexylmethane; 3,5,2'-triamino-2-methyl-dicyclohexylmethane (and mixtures); dibenzofuranamine; 1-aziridinepropanamine; 4-pyridinemethanamine; 2-pyridinamine; 1-(3-aminophenyl)-3-methyl-5-pyrazolone; pyrimidinamine; N-aminomorpholine and 2-aminobenzothiazole.

Amines which are particularly preferred are the following: propylamine; isopropylamine; n-butylamine; sec.-butylamine; tert.-butylamine; stearylamine; hexamethylenediamine; cyclohexylamine; 3,3,5-trimethyl-5-aminoethylcyclohexylamine; 4,4'-diamino-dicyclohexylmethane; aniline; p-chloroaniline; 3,4-dichloroaniline; m-tolylamine; p-methoxyaniline; 2,4-diaminotoluene; 2,6-diaminotoluene; 4,4'-diaminodiphenylmethane; 2,4'-diaminodiphenylmethane or commercial mixtures of the above-mentioned diaminotoluenes or diaminodiphenylmethanes.

Alcohols of the formula

in which $R_2$ is as defined above, are appropriate starting materials for the process of the present invention.

Examples of suitable alcohols are: methanol; ethanol; propanol; isopropanol; butanol; isobutanol; pentanol; isopentanol; hexanol; isohexanol; heptanol; isoheptanol; octanol; iso-octanol; nonanol; isononanol; decanol; iso-decanol; dodecanol; 2-ethylhexanol; β-chloroethanol; 2-ethylbutanol; hexadecanol; actadecanol; fatty alcohol mixtures; 2-methoxyethanol; 2-ethoxyethanol; 2-propoxyethanol; 2-butoxyethanol; 2-(2-methoxyethoxy)-ethanol; 2-(2-ethoxyethoxy)-ethanol; 2-(2-butoxyethoxy)-ethanol; cyclopentanol; cyclohexanol; methylcyclohexanol (and mixtures); cyclohexamethanol; 3,3,5-trimethylcyclohexanol; 4-tert.-butylcyclohexanol; 2-hydroxydecaline; borneol; isoborneol; 1-(2-hydroxyethoxy)-4-nitrobenzene; benzylalcohol; 2-phenylethanol; 2-(methoxyphenoxy)-ethanol (mixture); 1-phenylethanol; 3-phenyl-1-propanol and 4-methoxybenzylalcohol.

Particularly preferred alcohols are: methanol; ethanol; n-propanol; isopropanol; n-butanol; isobutanol; cyclohexanol; n-hexanol; 2-ethylhexanol; β-phenylethanol; glycol monomethylether; glycol monoethylether and diglycolmonomethylether.

N-unsubstituted urethanes of the formula:

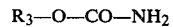

in which $R_3$ preferably has the same definition as $R_2$, are appropriate starting materials for the process of the present invention. $R_2$ and $R_3$ may represent the same or different radicals but it is most preferred that $R_2$ and $R_3$ be the same radicals. $R_3$ may also represent an aromatic hydrocarbon radical having a total from 6 to 15 carbon atoms which may be chloro or $C_1$- to $C_4$-alkyl substituted.

Examples of suitable N-unsubstituted urethanes are methyl, ethyl, n-propyl, isopropyl, n-butyl, n-decyl, n-octadecyl, cyclohexyl, benzyl, phenyl-4-chlorophenyl, 4-methylphenyl, 1-naphthyl or 4-tert.-butyl-carbamate or the corresponding carbamates derived from the above-mentioned alcohols. Particularly suitable and therefore preferred N-unsubstituted urethanes are: methyl-, ethyl-, n-propyl-, isopropyl-, n-butyl-, isobutyl-, cyclohexyl- or n-hexylcarbamate.

N-mono-substituted or N,N'-disubstituted ureas or polyureas may also be used as starting materials in addition to the N-unsubstituted urethanes described above. Appropriate ureas include N-mono-substituted or N,N'-disubstituted ureas or linear polyureas, particularly those which have terminal urethane or primary amino groups. The ureas or polyureas preferably have a maximum molecular weight of 2000. It is also preferred that the urea, urethane or amino groups be connected by hydrocarbon radicals. It is particularly preferred that the urea groups be substituted with hydrocarbon radicals which correspond to the hydrocarbon radical or hydrocarbon radicals of the reactant amine. It is also preferred that terminal urethane groups, where present, be substituted at the oxygen atom by the radical -$R_2$ corresponding to the alcohol used as the starting material. The total NH-CO-content of urea groups and urethane groups should be between 5 and 58% by weight, preferably between 10 and 58% by weight of the total weight of the urea.

Typical examples of suitable ureas or polyureas are: N-methyl-urea; N,N'-dimethylurea; N-ethyl urea; N-phenyl-urea; N,N'-diphenylurea; N,N-bis-(3-methylphenyl)-urea; N,N'-bis-(3,4-dichlorophenyl)-urea; N,N'-di-isobutylurea or compounds corresponding to the following formulae:

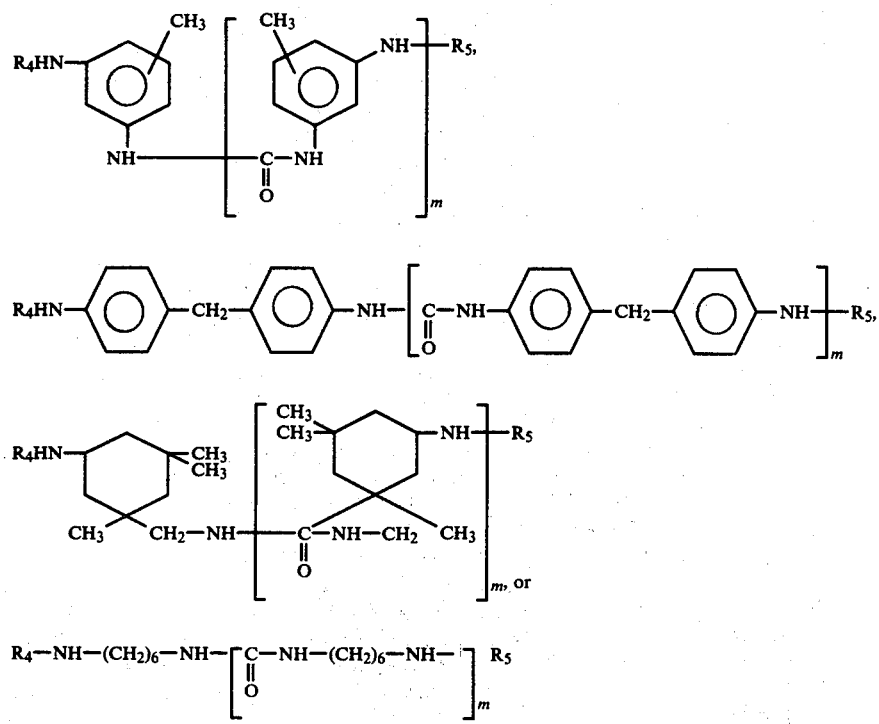

where m is a number from 1 to 10, $R_4$ and $R_5$ (which may be the same or different) represent H, $COOR_2$, $CONH_2$, or $CONHR_6$. $R_6$ represents a monofunctional radical of the type mentioned in the definition of $R_1$.

N,N'-disubstituted monoureas and bis-ureas are particularly preferred materials. Suitable ureas also include the N,N'-disubstituted ureas which are produced as by-products in the processes of U.S. Pat. Nos. 2,409,712 and 2,806,051, or the compounds produced according to Russ. Chem. Rev. 31 633 (1963) or Houben-Weyl XIV/2, 165 ff.

In carrying out the process of the present invention, the reactant amine (including amines which may be chemically bound in the urea-component, where this amine corresponds to the reactant amine), is generally used in 0.5 to 4 times, preferably 0.8 to 1.5 times and most preferably 0.9 to 1.1 times the stoichiometric quantity. The reactant alcohol-component (including the alcohol chemically bound in the N-unsubstituted urethane and optionally in the substituted urea, where this alcohol corresponds to the reactant alcohol component), is generally used in amounts which are 1 to 10 times, preferably 1.1 to 4 times, the stoichiometric quantity. The quantity of chemically bound alcohol is determined on the basis of the carbonyl groups present within urea groups or urethane groups. The urea compounds which may optionally be used, are generally used in quantities of from 0 to 300%, preferably 0 to 200%, by weight, based on the quantity of N-unsubstituted urethane.

The process according to the invention is preferably carried out with a catalyst. Suitable catalysts are any compounds which have a catalytic effect on the esterification reaction of carboxylic acids with alcohols. Such catalysts include: (i) organic or weak inorganic bases which are inert under the reaction conditions, (ii) Lewis acids and (iii) salts or complex compounds (particularly chelates) of transition metals.

The following are examples of suitable catalysts of group (i): tertiary amines such as tri-n-propylamine; triethylamine; tri-isopentylamine; diethylbenzylamine; N,N-dimethyl-benzylamine; hexahydrodimethylaniline; N-ethylpiperazine; diethyl(2-methoxypropyl)-amine; 2-(diethylaminoethyl)-phenylether; oxyethylmorpholine; N-(2-diethylaminoethyl)-benzamide; N-(2-diethylaminoethyl)-propionic amide; 1,4-diaza-(2,2,2)-bicyclooctane; N,N-dimethyl-4-aminopyridine; 1-azabicycloheptanes; 1-azabicyclooctanes; saturated polyheterocyclic amines; such as 3-methylconidine, 1-azabicyclo-(3,2,1)-octane, pyrrolizidines and quinuclidines; inorganic bases such as beryllium hydroxide, zinc oxide, magnesium-, barium- or calcium-hydroxide; basic alkali metal salts such as sodium carbonate, sodium sulphide, potassium carbonate or trisodium phosphate; and alkali metal salts of fatty acids or sulphonic acids.

Suitable catalysts (ii) are Lewis acids such as iron-II-chloride, iron-III-chloride, zinc chloride, tin-II-chloride, tin-IV-chloride, aluminum-chloride, zinc cyanide, borontrifluoride or borontrifluoride etherate.

Suitable catalysts of group (iii) are salts of transition metals, if they do not come under group (ii), and complex compounds particularly chelates of these metals such as cobalt-, manganese- or lead-naphthenates, iron oleates, or carbonyls, acetyl acetonates of iron, nickel, cobalt, zinc, lead, aluminum, manganese, magnesium, molybdenum, titanium, thorium, zirconium or vanadium; bis-(dibenzoylmethane)-copper; bis-(ethylacetoacetate)-copper or -iron; co-ordination compounds of titanium, zirconium, hafnium, thorium and manganese with β-diketones, β-ketoesters and β-hydroxyaldehydes; di-(2-ethylhexyl)-tin oxide; dioctyl tin oxide; zinc or tin salts of $C_1$-$C_{20}$ carboxylic acids such as zinc or tin(II)-naphthenate, hexoate, -palmitate, -stearate or -dimethylvalerate; acetates, chlorides, sulphates or octates of bi- or trivalent cobalt, of mono- or bivalent copper or bivalent lead.

Catalysts which are particularly suitable are: zinc chloride; zinc acetate; zinc octoate; zinc oxide, zinc cyanide, tin-II-chloride, tin-IV-chloride; dibutyl-tin dilaurate; cobalt triacetate; cobalt trichloride; cobalt trioctoate, copper(II)-acetate, copper-(I)-chloride; copper-(II)-sulphate; lead acetate or lead chloride. The quantity of catalyst used is generally in the range of from 1 ppm to 20% by weight, preferably from 100 ppm to 5% by weight, based on the total weight of the starting materials. Naturally, it will be practically advantageous to keep the concentration of the catalysts as low as possible. The optimum catalyst concentration depends on the nature of the starting material and on the activity of the particular catalyst. The optimum catalyst concentration can be readily determined by techniques known to those in the art.

The process of the present invention may be carried out under pressure or without application of external pressure. It is often appropriate to use pressure in the range of from 1 to 80 bar when the reaction temperature is higher than the boiling point of one or more of the starting materials. However, also in such case it is possible to carry out the process of the invention without pressure by heating a mixture of primary amines, N-unsubstituted urethanes and optionally N-mono- or N,N'-disubstituted ureas or polyureas to the reaction temperature and to add the low boiling alcohol at such a rate that the reaction mixture is maintained. The process according to the invention is generally carried out at a temperature in the range of from 120° C. to 350° C. and preferably from 130° to 300° C. and most preferably from 140° C. to 250° C.

The process according to the invention may be carried out with or without a solvent. Suitable solvents are solvents which are inert under the reaction conditions and have a boiling point of between 100° C. and 280° C., preferably between 150° C. and 250° C. Examples of appropriate solvents are: n-nonane; n-butylcyclohexane; decahydronaphthalene; n-undecane; n-dodecane; n-hexylcyclohexane; dipentene; 1-dodecane; isopropyl benzene; 1,3-diethylbenzene; indene; n-butyl benzene; tetralin; chlorobenzene; 4-chlorotoluene; 1,2-dichlorobenzene; 2,4-dichlorotoluene; 1,2,4-trichlorobenzene; 2-chloro-4-isopropyl-1-methylbenzene; anisole; cyclohexyl ethyl ether; diethylene glycol dimethyl ether; benzyl methyl ether; 4-methoxytoluene; para chloroanisole; di-n-hexyl ether; phenyl-n-propyl ketone; benzophenone; acetophenone; formamide; N,N-di-methylformamide; N,N-diethylformamide; N-methylformamide; dimethylacetamide; N-methylpyrrolidone; caprolactam; phenol; substituted phenols; sulpholane; hexamethylphosphoric acid triamide; dimethylsulphoxide; ethylene glycol monomethyl ether acetate; di-n-propylcarbonate; cyclohexyl acetate; diisobutylcarbonate; diethylene glycol monomethylether acetate; di-isoamylcarbonate; 2-ethylpyridine; N,N-dimethyl-2-methylaniline; N,N-dimethylaniline; N-methyl-N-ethylaniline; N,N-dimethyl-2-chloroaniline; N,N-diethylaniline; quinoline; nitrocyclohexane; nitrobenzene; 2-nitrotoluene; 2,4-dimethyl-1-nitrobenzene; acetonitrile; n-capronitrile; benzonitrile; toluenenitrile; diphenylether; tetramethylurea and phenyl acetonitrile. Polar solvents and mixtures thereof are preferred with ε-caprolactam being the most preferred.

It is often unnecessary to use such solvents, such as when a large excess of the reactant alcohol is used. Solvents are also unnecessary when preparing monourethanes from monoamines.

In carrying out the process of the present invention, the reactants are generally heated at the specified reaction temperature for 1 to 15, preferably from 2 to 10 hours. The process may be carried out by heating a mixture of all of the components or by heating a mixture of the alcohol, N-unsubstituted urethane and optionally a substituted urea to the required reaction temperature and then adding the primary amine to the heated mixture.

It is also possible when carrying out the process according to the invention, to use the N-unsubstituted urethane as the sole carbonyl group source. If the reaction is carried out using a reactant alcohol which is not the same as the chemically bound alcohol component of the unsubstituted urethane and the reactant alcohol has a higher boiling point than the chemically bound alcohol of the urethane, the alcohol present in the urethane is normally displaced and removed continuously during the reaction distillation. This displacement produces a disubstituted urethane having an alcohol component corresponding to the reactant alcohol. Where aromatic N-unsubstituted urethanes are used, the process is preferably carried out by using excess quantities of reactant alcohol. The phenol of the urethane is displaced by the reactant alcohol and the phenol formed may optionally be removed continuously although this is not necessary. In some cases, it may even be preferable to displace the alcohol or phenol of the reactant urethane with the reactant alcohol before the reactant amine is added.

In all of the variations of the process of the present invention, care must be taken to ensure that the evolving ammonia can escape.

The products of the process according to the invention may be worked up in any manner known to those in the art, such as distilling off the solvent and excess volatile starting materials. Such distillation should preferably be carried out after insoluble materials such as insoluble catalysts, have been removed (e.g., by filtration). The products of this process are generally recovered as the final fraction or as the distillation residue. The product urethanes may then be thermally dissociated into the isocyanate and alcohol from which they are derived in any manner known to those in the art.

Having thus described our invention, the following examples are given by way of illustration. The percentages given in these examples relate to percent by weight unless otherwise indicated.

EXAMPLE 1

A steel pressure vessel (with a volume capacity of 5 l and a maximum pressure capacity of 64 bar), having a stirrer and a heating jacket, was connected to a steel pressure distillation column so that the pressure vessel served as a sump container of the column. The column (nominal width 50 mm) was filled to a height of approximately 1 m with filling rings made of machine wire cloth (4 mm; steel) and was equipped with a spiral condenser at the top. A valve for the extraction of gases from the column was located above the top condenser.

838 g aniline, 676 g methyl carbamate, 1442 g methanol and 30.0 g anhydrous pulverized zinc chloride were introduced into the pressure vessel. The pressure vessel and the column were then purged with nitrogen. The mixture was subsequently heated (with stirring) to 190° C., and the top valve of the column was adjusted so that the pressure in the apparatus was just sufficient for the reactants to reach the reaction temperature. Ammonia which evolved was separated from the evaporating alcohol in the column and then removed from the top of the column. The reaction mixture was stirred for 6.5 hours at 190° C., while the ammonia which evolved was removed. The mixture was then cooled and removed from the pressure vessel after the pressure in the apparatus had been reduced. The mixture was filtered and then distilled at atmospheric pressure to remove the excess methanol. The product was then fractionally distilled at 0.2 m bar. 1120 g N-phenyl-carbamic acid methyl ester (82.3% of the theoretical yield) were collected and crystallized. The product had a melting point of 45° to 46° C.

EXAMPLE 2

1024 g aniline, 980 g ethyl carbamate and 1060 g ethanol (approximately 96%) were reacted in the apparatus described in Example 1 for 6.0 hours at 200° C. When the apparatus had cooled and the pressure had been reduced, the reaction mixture was removed, filtered and distilled to remove the excess ethanol. The product was then fractionally distilled at 0.4 m bar. 1373 g N-phenyl-carbamic acid ethyl ester (75.5% of the theoretical yield), were collected and crystallized. The product had a melting point of 51° to 52° C.

EXAMPLE 3

1024 g aniline, 980 g ethylcarbamate, 1060 g ethanol (approximately 96%) and 6.0 g zinc octoate were reacted in the apparatus described in Example 1 for 6.5 hours at 200° C. When the apparatus had cooled and the pressure had been reduced, the reaction mixture was removed, filtered and analyzed by high pressure liquid chromatography (HPLC). A yield of 1580 g (87% of the theoretical yield) of N-phenyl-carbamic acid-ethyl ester was obtained.

EXAMPLE 4

648 g of 3,4-dichloroaniline, 360 g methyl carbamate, 280 g N,N'-bis-(3,4-dichlorophenyl)-urea, 385 g methanol and 1600 g chlorobenzene were reacted in the apparatus described in Example 1 for 6.0 hours at 200° C. After the apparatus had cooled and the pressure had been reduced, the reaction mixture was removed, filtered and analyzed by high pressure liquid chromatography (HPLC). A yield of 990 g (80% of the theoretical yield) of N-(3,4-dichlorophenyl)-carbamic acid-methyl ester was obtained.

EXAMPLE 5

367 g of 2,4-diamino-toluene, 535 g ethyl carbamate, 580 g ethanol (approximately 96%) and 1500 g o-xylene were reacted in the apparatus described in Example 1 for 6.5 hours at 200° C. After the apparatus had cooled and the pressure had been reduced, the reaction mixture was removed, filtered and analyzed by high pressure liquid chromatography (HPLC). A yield of 540 g (68% of the theoretical yield), of 2,4-bis-(ethoxy carbonylamino)-toluene was obtained.

EXAMPLE 6

733 g of 2,4-diamino-toluene, 1069 g ethyl carbamate, 1160 g ethanol (approximately 96%) and 5.5 g zinc octoate were reacted in the apparatus described in Example 1 for 6.1 hours at 200° C. After the apparatus had cooled and the pressure had been reduced, the reaction mixture was removed, filtered and analyzed by high pressure liquid chromatography (HPLC). A yield of 1220 g (76% of the theoretical yield) of 2,4-bis-(ethoxy carbonylamino)-toluene was obtained.

EXAMPLE 7

275 g of a polyurea mixture based on 2,4-diamino-toluene having terminal amino tolyl groups (average molecular weight: 1500) were introduced into the apparatus described in Example 1. 513 g of 2,4-diamino-toluene, 933 g ethyl carbamate and 1250 g ethanol (approximately 96%) were subsequently added. The mixture was reacted for 6.0 hours at 200° C. After the apparatus had cooled and the pressure had been reduced, the reaction mixture was removed, filtered and analyzed by high pressure liquid chromatography (HPLC). A yield of 1100 g (68% of the theoretical yield) of 2,4-bis-(ethoxy carbonylamino)-toluene was obtained.

EXAMPLE 8

52 g of 4,4'-diamino-diphenyl methane, 990 g isopropyl-carbamate, 1010 g isopropanol and 6.0 g zinc octoate were reacted in the apparatus described in Example 1 for 6.5 hours at 200° C. After the apparatus had cooled and the pressure had been reduced, the reaction mixture was removed, filtered and analyzed by high pressure liquid chromatography (HPLC). A yield of 1300 g (73% of the theoretical yield) of 4,4'-bis-(isopropoxy-carbonylamino)-diphenyl methane was obtained.

EXAMPLE 9

766 g of isophorone diamine (3-aminomethyl-3,5,5-trimethyl-cyclohexylamine), 1054 g of n-butyl carbamate and 1000 g n-butanol were reacted in the apparatus described in Example 1 for 4.0 hours at 180° C. After the apparatus had cooled and the pressure had been reduced, the reaction mixture was removed, filtered and analyzed by high pressure liquid chromatography. A yield of 1350 g (81% of the theoretical yield) of 1-(n-butoxy-carbonylamino)-3,3,5-trimethyl-5-(n-butoxy carbonylamino-methyl)-cyclohexane was obtained.

EXAMPLE 10

210 g (1 mol) of 4,4'-diaminodicyclohexyl methane, 186.9 g (2.1 mols) of carbamic acid ethyl ester, 488 g (4 mols) β-phenyl ethanol and 0.9 g zinc octoate were heated under reflux to a sump temperature of 200° C. so that the resulting ethanol was continually distilled off. The reaction mixture was kept at 200° C. for another 8 hours and excess β-phenyl ethanol was then distilled off at 0.1 torr and 110° C. The residue (486 g) hardened into a solid mass which when cooled was examined by IR and NMR. These analyses indicated that 4,4'-bis-[(2-phenylethoxy)-carbonylamino]-dicyclohexyl methane having a purity of better than 90% was present in an amount which was greater than 86% of the theoretical yield.

EXAMPLE 11

390 g (3 mols) of 2-ethyl hexanol, 186.9 g (2.1 mols) of carbamic acid ethyl ester and 1.5 g zinc octoate were heated for 3 hours under reflux in a manner such that the resulting ethanol was continually distilled off. 116 g (1 mol) of hexamethylene diamine were then added dropwise over a period of 5 hours while the mixture was maintained at 200° C. The resultant mixture was subsequently stirred for another 4 hours. Addition of 300 g of ε-caprolactam to the mixture, would permit faster addition of the amine without formation of a precipitate.

The reaction mixture was concentrated by subjecting it to a pressure of 0.1 torr and a temperature of 115° C. The fraction of the concentrated mixture which was insoluble in acetic acid ethyl ester was then removed. A slowly hardening mass (361 g) was left. Analysis by IR and NMR spectroscopy indicated that 1,6-bis[(2-ethyl-hexoxy)-carbonylamino]-hexane which was approximately 90% pure had been formed in an amount which was 76% of the theoretical yield.

EXAMPLE 12

366 g (3 mols) of β-phenyl ethanol and 186.9 g (2.1 mols) carbamic acid ethyl ester were heated with 1.5 g zinc octoate under reflux for 2 hours in a manner such that the ethanol evolved was continuously distilled off. 116 g (1 mol) hexamethylene diamine was then added dropwise over a period of 3.5 hours at 200° C. The resultant mixture was subsequently stirred for another 6 hours. Excess β-phenyl ethanol was then distilled off at a temperature of 130° C. and a pressure of 0.1 torr. The highly viscous, slowly hardening residue (397.6 g) still contained approximately 10% β-phenyl ethanol according to IR and NMR analysis. This residue which was 1,6-bis-[(phenyl ethoxy)-carbonylamino]-hexane had been formed in an amount which was 87% of the theoretical yield.

EXAMPLE 13

71.5 g (0.5 mol) of carbamic acid cyclohexyl ester, 46.5 g (0.5 mol) aniline, 100 g (0.1 mol) cyclohexanol and 0.8 g cobalt acetate were heated for 6 hours under reflux in a manner such that the temperature rose slowly to 185° C. The yield of O-cyclohexyl-N-phenylurethane was determined by means of high pressure liquid chromatography to be 80% of the theoretical yield.

EXAMPLE 14

89 g (1 mol) of carbamic acid ethyl ester, 93 g (1 mol) of aniline, 136 g (1 mol) phenylurea and 25 g (2.5 mols) cyclohexanol were heated under reflux with 0.8 g of 2,3,4,6,7,8,9,10-octahydro-pyrimido-(1,2-a)-azepine. The condenser was preliminarily heated to 90° C. so that the ethanol formed was continuously distilled off. The temperature of the reaction mixture rose to 200° C. within 5 hours and was maintained at that temperature while being stirred for 6 hours. The yield of O-cyclohexyl-N-phenyl urethane was determined by high pressure liquid chromatography to be 82.5% of the theoretical yield (based on the carbonyl group equivalents used).

EXAMPLE 15

301.4 g (2 mols) carbamic acid phenyl ester, 204.6 g (2.2 mols) aniline and 300 g (3 mols) cyclohexanol were heated for 7 hours under reflux. Little ammonia evolved after 4 hours. The solution was concentrated by subjecting it to a temperature of 100° C. and pressure of 0.3 torr. 72.7% of theoretical yield of O-cyclohexyl-N-phenyl urethane was determined to be present in the residue by high pressure liquid chromatography.

EXAMPLE 16

89 g (1 mol) carbamic acid ethyl ester, 93 g (1 mol) aniline, and 610 g (5 mols) β-phenyl ethanol were heated with 0.6 g zinc octoate under reflux for 5 hours. The ethyl alcohol evolved was continuously distilled off. The temperature rose from 170° C. to 222° C. and the evolution of ammonia ceased towards the end of the reaction.

N-phenyl-O-(β-phenylethyl)-urethane was produced in an amount which was 87.6% of the theoretical yield (determined by HPLC).

EXAMPLE 17

178 g (2 mols) carbamic acid ethyl ester, 186 g (2 mols) aniline and 240 g (2.4 mols) cyclohexanol were heated with 0.6 g zinc octoate under reflux for 7 hours, so that while the evolving ammonia was released, the temperature rose steadily to 220° C. The ethanol formed was continuously distilled off. After adding 60 g cyclohexanol, the reaction mixture was heated under reflux for another 2 hours. The O-cyclohexyl-N-phenyl urethane formed was determined by HPLC to be 91.4% of the theoretical amount.

EXAMPLE 18

150 g (2 mols) carbamic acid methyl ester, 186 g (2 mols) aniline, 240 g (2.4 mols) cyclohexanol and 0.8 g zinc octoate were heated under reflux for 7 hours, so that the methanol was continuously distilled off. After the sump temperature had reached 200° C. and evolution of ammonia had substantially ceased, the reaction mixture was mixed with 0.6 mol cyclohexanol and heated at 200° C. for another 2.5 hours. The yield of O-cyclohexyl-N-phenyl urethane was determined to be 90% of the theoretical yield by means of high pressure liquid chromatography (HPLC).

EXAMPLE 19

133.5 g carbamic acid ethyl ester (1.5 mol), 107 g of 3-amino-toluene (1 mol), 120 g of 3,3'-dimethyl-N,N'-diphenyl urea (0.5 mol) and 100 g cyclohexanol (1 mol) were stirred together in a 1 liter vessel and subsequently mixed with 2 ml zinc octoate and heated to 165° C. The reactor temperature was slowly raised. 300 g cyclohexanole (3 mols) were added dropwise over a period of 2 hours at an internal temperature of from 180° to 185° C. The internal temperature rose to 194° C. within 4 hours. The ethyl alcohol which was produced during the reaction was distilled off continuously. The excess cyclohexanol was removed under vacuum and the residue was distilled off and recrystallized in petroleum benzene. 370 g N-(m-tolyl)-O-cyclohexyl urethane (79% of the theoretical yield) having a boiling point of 134° to 138° C. at 0.5 m bar and a melting point of 82° to 84° C. (from petroleum benzene) were produced.

EXAMPLE 20

74 g carbamic acid ethyl ester (0.83 mol), 152 g 3-amino-di-benzofuran (0.83 mol), 102 g n-hexanol (1 mol) and 2 g zinc chloride were introduced into a 500 ml quadruple neck flask equipped with a stirrer, a thermometer, a dropping funnel and a steam heated reflux condenser. The mixture was then slowly heated to 200° C. At this temperature, 25.4 g n-hexanol (0.25 mol) were added dropwise, while the ethyl alcohol distilled off. The reaction mixture was then stirred for 10 hours at 200° C. The reaction product was recrystallized from petroleum benzene. 216 g of N-(3-dibenzofuranyl)-O-n-hexyl urethane (83.5% of the theoretical yield) having a melting point of 103° to 104° C. were recovered.

EXAMPLE 21

137 g carbamic acid phenyl ester (1 mol), 101 g of n-hexyl amine (1 mol), 150 g cyclohexanol (1.5 mol) and 2 ml zinc octoate were heated. The evolution of ammonia commenced at 155° to 160° C. The temperature rose to 200° C. within 2 hours and the reaction mixture was maintained at that temperature for 3 hours. The reaction mixture was then fractionally distilled.

The product was identified by IR and NMR analysis to be N-(n-hexyl)-O-cyclohexyl urethane. 185 g (91% of the theoretical yield) of the product urethane having a boiling point of 130° to 132° C. at 0.26 torr were recovered.

EXAMPLE 22

51.8 g of the compound:

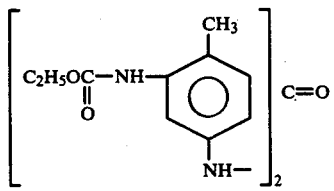

(0.125 mol), 61 g of 2,4-diamino-toluene (0.5 mol), 100 g carbamic acid ethyl ester (1.125 mols), 200 g cyclohexanol (2 mols) and 3 g thallium chloride were heated to 140° C. The ethyl alcohol formed was distilled off and the reaction temperature was raised to 200° C. and maintained at that temperature for 7 hours. Any cyclohexanol remaining in the mixture was distilled off under a water jet vacuum and the residue was subsequently mixed with a little acetic ester. The reaction mixture crystallized completely overnight. 284 g of 2,4-bis-(cyclohexoxy carbonylamino)-toluene (76% of the theoretical yield) having a melting point of 156° C. (from toluene) were produced.

EXAMPLE 23

234 g (2 mols) carbamic acid butyl ester, 186 g (2 mols) aniline, 408 g (3 mols) monophenyl urea, 74 g (1 mol) n-butanol and 5 g titanium acid tetrabutyl ester were heated in a 2 l quadruple neck flask equipped with a stirrer, contact thermometer, reflux condenser and dropping funnel. Ammonia started to evolve vigorously at temperatures above 130° C. The ammonia gas was collected in dilute sulphuric acid. While 148 g (2 mols) n-butanol were added dropwise, the temperature rose to 175° C. over a period of 2 hours. 74 g (1 mol) n-butanol were then added over a period of 2 hours during which the temperature was maintained at 175° C. A total of 4.8 mols (96% of the theoretical amount) of ammonia were evolved. 86% of the crude product (1020 g) was determined to be N-butyl-urethane by high pressure liquid chromatography. This yield was 91% of the theoretical yield.

EXAMPLE 24

692 g (4 mols) carbamic acid-2-ethyl hexyl ester, 390 g (3 mols) 2-ethyl hexanol, 344 g (2 mols) of N,N'-diisobutyl-urea and 5 g zinc dioctoate were introduced into a 2 l quadruple neck flask equipped with a stirrer, a contact thermometer, a reflux condenser and a dropping funnel. The mixture was heated to 180° C. and ammonia which started to evolve rapidly was collected in dilute sulphuric acid. 146 g isobutyl amine were then added dropwise over a period of 2 hours to the reactor maintained at 180° C. The result of this addition was an increase in the evolution of ammonia. The reactor temperature was then gradually raised to 220° C. over a period of 3 hours. A total of 3.8 mols of ammonia (95% of the theoretical amount) evolved. The mixture (1505 g) was then fractionated by distillation. 627 g (2.74 mols) of N-isobutyl-O-(2-ethylhexyl)-urethane having a boiling point of 116° C. at 0.2 mm were obtained. The product urethane was recovered in an amount which corresponded to 4.92 mols or 82.7% of the theoretical yield, based on the total mixture.

EXAMPLE 25

85,4 g (0,7 mols) of 2,4-diamino toluene, 36,6 g (0,3 mols) of 2,6-diamine toluene, 180 g (2,4 mols) of carbamic acid methyl ester, 250 g (2,5 mols) of cyclohexanol and 0,2 g of zinc octoate are heated to reflux temperature. Simultaneously methanol which is being formed is continuously distilled off. When the reaction temperature has reached 180° C. cyclohexanol is slowly dropped into the reaction mixture so that the reaction temperature is maintained at 180° C. After 14 hours 2,4- and 2,6-bis(cyclohexoxycarbonylamino)-toluene is formed in an amount which corresponds to 93% of the theoretical yield (HPLC analysis).

EXAMPLE 26

480 g (4 mols) of diethylene glycol monomethylether, 222,5 g (2,5 mols) of carbamic acid ethylester and 1 g of zinc octoate are heated for 1 hour to 200° C. Simultaneously ethanol which is being formed is continuously distilled off. Subsequently 198 g (1 mol) of 4,4'-diaminodiphenyl methane are added dropwise during 2 hours. The reflux temperature is simultaneously maintained at 200° C. by the addition of diethylene glycol dimethylether. After a reaction time of 8 hours 4,4'-bis-[2-(2-methoxyethoxy-)-ethoxycarbonylamino]-diphenyl methane is formed in an amount which corresponds to 92,5% of the theoretical yield (HPLC analysis).

What is claimed is:

1. A process for the preparation of N,O-disubstituted urethanes by reacting primary amines and alcohols with organic compounds having carbonyl groups in the temperature range of from 120° to 350° C., characterized in that N-unsubstituted urethanes and at least one compound taken from the group consisting of N-monosubstituted ureas, N,N'-disubstituted ureas and polyureas are used as the organic compounds having carbonyl groups.

2. The process of claim 1, wherein the reaction is carried out in the presence of a polar solvent.

3. The process of claim 1, wherein the reaction is carried out in the presence of esterification catalysts for carboxylic acids.

4. The process of claim 1, wherein the reaction is carried out in a polar solvent.

5. The process of claim 4, wherein the alcohol used as the reactant is present in excess to act as the solvent.

6. The process of claim 4, wherein ε-caprolactam is used as the solvent.

* * * * *